United States Patent [19]

Moro et al.

[11] 4,287,352
[45] Sep. 1, 1981

[54] PROCESS FOR PREPARING ALPHA-THIENYLACETIC ACID, ESTERS AND SALTS THEREOF

[75] Inventors: Alessandro Moro, Pernate; Marco Foà; Luigi Cassar, both of Novara, all of Italy

[73] Assignee: Montedison, S.p.A., Milan, Italy

[21] Appl. No.: 60,225

[22] Filed: Jul. 24, 1979

Related U.S. Application Data

[63] Continuation of Ser. No. 888,396, Mar. 20, 1978, abandoned.

[51] Int. Cl.$^3$ ............................................. C07D 333/16
[52] U.S. Cl. ........................................................ 549/79
[58] Field of Search .......................................... 549/79

[56] References Cited

PUBLICATIONS

Chem. Abstracts (1964), 61, 13149.
Journal of Org. Chem., vol. 42, No. 22, 1972, pp. 3522–3524.
Chem. Abstracts (1965), 62, 38979.
JACS /91:19/ Sep. 23, 1970, pp. 5752–5753.
Org. Synth. Collective, vol. 3, pp. 197–199.
Beilstein, E. III/IV, 18, p. 268.
Weil et al., "Carbonylation of Org. Hal", Org. Synth. Via Metal Carbonyls, vol. II, (1977), pp. 517–543.

*Primary Examiner*—Alan Siegel
*Attorney, Agent, or Firm*—Stevens, Davis, Miller & Mosher

[57] ABSTRACT

A process is disclosed for preparing alpha-thienylacetic acid, alkyl esters and salts thereof by carbonylation of 2-chloromethylthiophene, characterized in that 2-chloromethylthiophene and carbon monoxide are reacted under atmospheric pressure and at a temperature ranging from 0° to 60° C., in an aqueous-alcoholic solution in the presence of a catalyst selected from the class consisting of $Co_2(CO)_8$, $MCo(CO)_4$ where M is selected from the class consisting of Na and K, and a system comprising a cobalt salt (such as cobaltous chloride), a ferro-manganese alloy and at least one sulphur-containing promoter (such as the alkaline sulphides and thiosulphates), and in the presence of an inorganic base, and the separating the alpha-thienylacetic acid from the resulting salt and/or ester obtained.

7 Claims, No Drawings

PROCESS FOR PREPARING ALPHA-THIENYLACETIC ACID, ESTERS AND SALTS THEREOF

This is a continuation of application Ser. No. 888,396 filed Nov. 20, 1978 now abandoned.

This invention relates to the synthesis of alpha-thienyl-acetic acid or 2-thiopheneacetic acid, or the esters and/or salts thereof by carbonylation of 2-chloromethylthiophene. More particularly, the present invention relates to a process for preparing alpha-thienylacetic acid, its alkyl esters and/or salts thereof via synthesis from carbon monoxide and 2-chloromethylthiophene, catalyzed by a catalyst system based on cobalt carbonyl complexes.

As is well known, alpha-thienylacetic acid is generally employed as an intermediate for organic syntheses, such as, for example, the one leading to the preparation of compounds protecting vegetable crops (e.g., wheat, cereals) against damage caused by weed-killers, or to the preparation of pharmaceutical products, such as antibiotics in general, for example cephalotin, which is the sodium salt of 7-(thiophene-2-acetamido)-cephalosporanic acid (see Merck No. 1939).

The preparation of alpha-thienylacetic acid is carried out, according to the prior art, by reacting 2-chloromethylthiophene with alkaline cyanides and thereafter saponifying the resulting nitrile to alpha-thienylacetic acid; or by reacting 2-acetylthiophene with ammonium polysulphide to alpha-thienylacetamide, which is then saponified to alpha-thienylacetic acid. Alphathienylacetic acid can be also prepared by the acid alcoholysis of the intermediate 1-methylsulphinyl-1-methylthio-2-thiophenethylene.

The methods cited above are non-catalytic polystage methods that are relatively complicated due to the utilization of reagents difficult to be found and/or handled (e.g., cyanides) and involving high operating costs, which render such methods scarcely attractive for industry.

On the other hand, the use of catalyst systems based on metal-carbonyl complexes for the carbonylation of benzyl halides in an alkaline medium in order to obtain the corresponding acids is also known.

Nevertheless, and so far as is known, none of the foregoing techniques has been extended (or was known to be extensible) to the carbonylation of heterocyclic and/or sulphur-containing nuclei exerting a typical disturbing action on the trend of catalysis reactions with transition metals.

In the case of 2-chloromethylthiophene, its reactivity towards methanol, a carbonylation solvent, is about 2000 times higher than that of benzyl chloride.

Thus it is an object of the present invention to provide a simple and economic process for preparing alpha-thienylacetic acid, capable of obviating the above-cited drawbacks by offering the possibility of obtaining alpha-thienylacetic acid by the catalytic carbonylation of 2-chloromethylthiophene at atmospheric pressure, including preparing the catalyst "in situ" under the same conditions as the synthesis, with practically quantitative yields, at a high reaction rate, and in one step only.

This and still further objects that will more clearly appear to those skilled in the art from the following description, are achieved, according to this invention, by a process for preparing alpha-thienylacetic acid, as well as esters and salts thereof, characterized in that 2-chloromethylthiophene is reacted with carbon monoxide in the presence of a catalyst selected from amongst cobalt carbonyl ($Co_2(CO)_8$) and the alkaline salts thereof having the formula $MCo(CO)_4$, and a catalyst system consisting or consisting essentially of a cobalt salt, a ferro-manganese alloy, and sulphurated promoters in a hydroalcoholic solvent and in the presence of an inorganic base, at atmospheric pressure and at a temperature ranging from 0° to 60° C., and then, according to conventional methods, separating the alpha-thienylacetic acid from the ester and/or salt obtained. In the foregoing, M is a metal selected from Na and K.

The reaction may be schematically represented by the following equations:

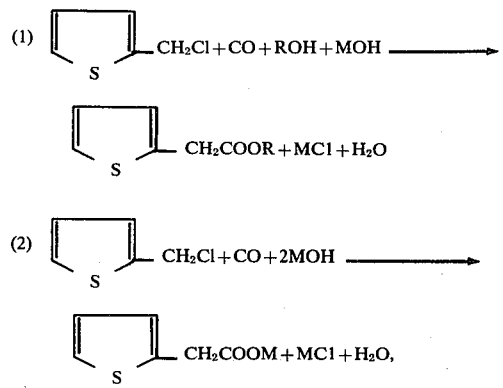

wherein R is lower alkyl such as methyl or ethyl; M is an alkaline inorganic base such as NaOH, KOH, etc., or CaO may be employed.

Free alpha-thienylacetic acid may then be easily obtained by simple shifting with strong mineral acids, such as HCl, $H_2SO_4$, etc., or by hydrolysis of the esters.

From reactions (1) and (2) it is apparent that, depending on the amount of inorganic base (MOH) present [1 mole in reaction (1) and 2 moles in reaction (2)], it is possible to selectively obtain the alkaline salts (Na and K) or the methyl or ethyl esters. ROH is always present as the hydroalcoholic solvent.

The reaction is conducted in the presence of a catalyst selected from amongst cobalt carbonyl $Co(CO)_8$, alkaline cobalt carbonylate $MCo(CO)_4$ wherein M has the meaning specified hereinbefore, and a further catalyst system composed of a cobalt salt, a ferro-manganese alloy and sulphurated promoters.

The first two are known compounds, obtainable according to conventional techniques. For instance, $Co_2(CO)_8$ may be prepared by reacting cobalt carbonate with a gaseous mixture of CO and $H_2$ under pressure in petroleum ether, while $NaCo(CO)_4$ may be prepared by reducing $Co_2(CO)_8$ with a metal sodium amalgam at 1% in ether.

Finally, the catalyst system comprising a cobalt salt, a ferro-manganese alloy, and sulphurated promoters, may be prepared from a cobalt salt, such as, for example, chloride, sulphide, bromide, etc.; an Fe/Mn alloy (containing about 80% of Mn), and sulphurated promoters, in methyl or ethyl alcohol, or in mixtures thereof with water, under atmospheric pressure of carbon monoxide, at temperatures between 10° and 80° C., and preferably between 25° and 35° C. The cobalt salt concentration in the solution preferably is between 0.3 and 1 mole/liter. From 1 to 2 moles of Mn in the form of Fe/Mn alloy are employed for each mole of cobalt salt. The Fe/Mn alloy is previously ground in order to get it to pass through a screen of at least 5000 mesh/cm$^2$.

The preferred sulphurated promoters are sodium sulphide and sodium thiosulphate, which are employed in amounts of from 0.01 to 0.1 mole per mole of cobalt salt. The mixture is kept under intense stirring for 2-3 hours.

The catalytic mixture thus obtained is diluted from 4 to 12 times with a further amount of methyl or ethyl alcohol and if desired water too. The water concentration in the final reaction mixture ranges from 0 to 35%, and preferably from 0 to 20%.

The reaction temperature ranges from 0° to 60° C., and preferably from 20° to 35° C.

Oxides or hydroxides of alkaline metals, such as CaO, NaOH, KOH, etc. are used as bases.

If use is made of hydroxides soluble in the reaction hydroalcoholic medium (NaOH, KOH), the addition of same must be carried out gradually, making sure by means of e.g. a glass electrode that the pH does not exceed a value of about 12. CaO can be wholly added at the beginning. Higher pH values may lead to lower yields of the desired product due to formation of thienylmethylether.

Reaction times of approximately 2-5 hours are sufficient for completing the reaction.

The use of methyl or ethyl alcohol alone or in admixture with water permits more easily the neutralization of acidity developing during the reaction and therefore better protecting the catalytic system.

At the conclusion of the reaction the methyl or ethyl ester of alpha-thienylacetic acid is obtained, optionally also partially salified as the alkaline salt.

By distillation of the solvent alcohol in a basic medium it is possible to completely saponify the ester to the alkaline salt of acid, wherefrom by acidification, preferably with HC1, alpha-thienylacetic acid is liberated, which is then extracted with an organic solvent (e.g. ether), and separated, etc., according to per se conventional methods.

As an alternative, from the methyl or ethyl ester of alphathienylacetic acid it is possible directly to obtain the free acid by acid hydrolysis, extraction, etc. without first converting it to alkaline salt, according to per se known methods.

According to one efficient mode of procedure, the process of the present invention is conducted as follows:

A catalytic mixture is prepared as described hereinbefore, or a solution of $Co_2(CO)_8$ or of $NaCo(CO)_4$ in the hydro-alcoholic solvent. It is then brought to a temperature of 0°-60° C., and preferably 20°-35° C. Carbon monoxide is maintained in contact with the intensely stirred solution at about 1 kg/cm$^2$ absolute. 2-chloromethylthiophene is added over a period of approximately 2 to 5 hours in amounts ranging from 5 to 20%, and preferably from 10 to 15% in respect to the weight of solvent. Better results are achieved by keeping the neutralizing base in excess in respect to the 2-chloromethylthiophene, by gradually adding such base.

At the conclusion of the reaction the solvent is recovered by distillation in a basic medium. From the alkaline salt of the resulting alpha-thienylacetic acid it is possible to readily liberate, by the addition of a strong acid, and preferably hydrochloric acid, the alpha-thienylacetic acid, which may then be readily extracted with an organic solvent, etc., in the usual manner.

Owing to the mild operating conditions, the process of the present invention appears particularly attractive from the economic point of view.

Further advantages consist in the catalytic nature of the reaction and in the high yields.

The present invention will be illustrated still further in detail by the following examples, which however are given merely for illustrative purposes:

EXAMPLE 1

45 ml of methanol, 5 g of $CoCl_2.6H_2O$, 0.10 g of sodium sulphide and 0.37 g of sodium thiosulphate were introduced, under a CO head, into a 0.5-liter flask equipped with a stirrer, a funnel for liquids, a funnel for solids, a thermometer, a water cooler, and a pH-meter. Stirring was started (500 r.p.m.) and 2.25 g of an Mn/Fe alloy (Mn=80%), ground up to over 10,000 mesh/cm$^2$, were introduced. Absorption of CO began at once and continued for 3 hours. A total of 1.6 Nl of CO (85% of the theoretical value) were absorbed. The catalyst suspension in methanol thus obtained was then utilized as follows:

210 ml of methanol were added to the catalyst methanol suspension thus obtained. Stirring was started, the temperature was brought to 25° C., and in 5 hours 20 g of chloromethylthiophene as well as 18 g of calcium oxide were added, keeping the mixture under a carbon monoxide head. On completion of the addition the mixture was maintained under stirring for another hour.

3100 ml of carbon monoxide were absorbed in the aggregate. 270 ml of water were added in two portions to the mixture, and 310 ml of a water-methanol mixture containing 10% of water useful for the succeeding tests were recovered by distillation.

25 ml of concentrated hydrochloric acid (37 g of HCl in 100 ml) were then added to the distillation residue, whereupon it was extracted with three 200-ml portions of ethyl ether. The aqueous phase was removed and the collected organic phases were evaporated to dryness, thus obtaining 15.4 g of alpha-thienyl-acetic acid.

Yield: 72% in respect of the chloromethylthiophene charged. Melting point: 64° C.

EXAMPLE 2

12 ml of a catalyst suspension obtained as described above in Example 1, 60 ml of methyl alcohol, and 6 ml of $H_2O$, were introduced into a 250-ml flask, equipped with a stirrer, a charging funnel, a thermometer, and a water cooler, and connected to a graduated 500-ml burette containing CO under a water head.

After bringing the mixture to 20° C., 3.3 g of 2-chloromethylthiophene were dropped thereinto over a period of 5 hours.

This time the pH value was adjusted to between 10 and 12 by addition of 23% NaOH in aqueous solution.

6 ml of soda and 300 ml of CO were required in the aggregate.

After saponification and extraction with ether, 1.7 g of the desired acid were obtained: the yield was 48% in respect of the 2-chloromethylthiophene charged.

EXAMPLE 3

By operating with the same apparatus and according to the same procedures as in Example 2, a mixture having the composition specified below was reacted at a temperature of 26° C.:

12 ml of the same catalyst suspension,
25 ml of methyl alcohol,
1 ml of water, and
9.0 g of CaO.
10 g of 2-chloromethylthiophene were then dropped in over a period of about 6 hours. At the conclusion of this addition, the whole was left under stirring for another hour. 1600 ml of CO were absorbed in the aggregate.

After saponification and extraction with ether, 7.6 g of the desired acid were obtained, the yield being 73% in respect of the 2-chloromethylthiophene charged.

EXAMPLE 4

By following the same procedure as in Example 2, the following mixture was reacted:
 0.8 g of NaCo(CO)$_4$,
 25 ml of methyl alcohol,
 1 ml of water, and
 4 g of CaO.

While maintaining a temperature of 30° C., 5.5 g of chloromethylthiophene where added over a period of 3 hours.

By operating according to the procedures previously described, 4.0 g of the desired alpha-thienylacetic acid were obtained (yield=70%).

EXAMPLE 5

Following the same procedures as in Example 2, the following mixture was reacted:
 11 g of Co$_2$(CO)$_8$,
 25 ml of methyl alcohol,
 1 ml of water, and
 4 g of CaO.

The further procedure was as in Example 4, whereupon 3.8 g of alpha-thienylacetic acid were obtained (yield=66%).

What is claimed is:

1. A process for preparing alpha-thienylacetic acid, alkyl esters and salts thereof by carbonylation of 2-chloromethylthiophene, characterized in that 2-chloromethylthiophene and carbon monoxide are reacted under atmospheric pressure and at a temperature ranging from 0° to 60° C., in an aqueous-alcoholic solution in the presence of a catalyst selected from the class consisting of (a) Co$_2$(CO)$_8$, (b) MCo(CO)$_4$ where M is selected from the class consisting of Na and K, and (c) a system comprising a cobalt salt, a ferromanganese alloy and at least one sulphur-containing promoter, and in the presence of an inorganic base, and then separating the alpha-thienylacetic acid from the resulting salt and/or ester obtained.

2. A process according to claim 1, characterized in that the reaction temperature is between 20° and 35° C.

3. A process according to claim 1, characterized in that the aqueous-alcoholic solution of the final mixture consists essentially of methyl alcohol and/or ethyl alcohol and water in amounts ranging from 0 to 35%.

4. A process according to claim 3, wherein the methyl alcohol and/or ethyl alcohol and water range from 0 to 20%.

5. A process according to claim 1, characterized in that the cobalt salt is cobaltous chloride.

6. A process according to claim 1, characterized in that the sulphur-containing promoters are selected from the class consisting of alkaline sulphides and alkaline thiosulphates.

7. A process according to claim 1, characterized in that the inorganic base is selected from the class consisting of CaO, NaOH and KOH employed in amounts equal to at least one mole for each mole of 2-chloromethylthiophene.

* * * * *